United States Patent
Nguyen et al.

(10) Patent No.: US 10,392,399 B2
(45) Date of Patent: Aug. 27, 2019

(54) CRYSTALLINE FORMS OF THERAPEUTIC COMPOUNDS AND USES THEREOF

(71) Applicant: Kala Pharmaceuticals, Inc., Waltham, MA (US)

(72) Inventors: Minh Ngoc Nguyen, Dorchester, MA (US); Winston Zapanta Ong, Stoneham, MA (US)

(73) Assignee: kala pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 15/694,383

(22) Filed: Sep. 1, 2017

(65) Prior Publication Data

US 2018/0065979 A1 Mar. 8, 2018

Related U.S. Application Data

(60) Provisional application No. 62/385,155, filed on Sep. 8, 2016.

(51) Int. Cl.
*C07D 491/107* (2006.01)

(52) U.S. Cl.
CPC ...... *C07D 491/107* (2013.01); *C07B 2200/13* (2013.01)

(58) Field of Classification Search
None
See application file for complete search history.

(56) References Cited

U.S. PATENT DOCUMENTS

| | | |
|---|---|---|
| 4,910,225 A | 3/1990 | Ogawa et al. |
| 4,996,335 A | 2/1991 | Bodor |
| 5,190,956 A | 3/1993 | Afonso et al. |
| 5,364,884 A | 11/1994 | Varma et al. |
| 5,442,039 A | 8/1995 | Hefner, Jr. et al. |
| 5,486,512 A | 1/1996 | Gregor |
| 5,518,187 A | 5/1996 | Bruno et al. |
| 5,534,259 A | 7/1996 | Zalipsky et al. |
| 5,580,870 A | 12/1996 | Barker et al. |
| 5,718,388 A | 2/1998 | Czekai et al. |
| 5,747,061 A | 5/1998 | Aselem et al. |
| 5,773,476 A | 6/1998 | Chen et al. |
| 5,862,999 A | 1/1999 | Czekai et al. |
| 5,922,357 A | 7/1999 | Coombes et al. |
| 6,046,208 A | 4/2000 | Adams et al. |
| 6,106,819 A | 8/2000 | Sucher |
| 6,153,607 A | 11/2000 | Pflugfelder et al. |
| 6,153,617 A | 11/2000 | Bridges |
| 6,165,509 A | 12/2000 | Hoffman et al. |
| 6,197,346 B1 | 3/2001 | Mathiowitz et al. |
| 6,217,908 B1 | 4/2001 | Mathiowitz et al. |
| 6,235,313 B1 | 5/2001 | Mathiowitz et al. |
| 6,264,981 B1 | 7/2001 | Zhang et al. |
| 6,288,082 B1 | 9/2001 | Wissner et al. |
| 6,365,187 B2 | 4/2002 | Mathiowitz et al. |
| 6,372,246 B1 | 4/2002 | Wei et al. |
| 6,627,228 B1 | 9/2003 | Milstein et al. |
| 6,706,289 B2 | 3/2004 | Lewis et al. |
| 7,153,524 B2 | 12/2006 | Yoshihara et al. |
| 7,262,201 B1 | 8/2007 | Hennequin et al. |
| 7,534,449 B2 | 5/2009 | Saltzman et al. |
| 7,550,441 B2 | 6/2009 | Farokhzad et al. |
| 7,795,237 B2 | 9/2010 | Ahmed et al. |
| 7,842,232 B2 | 11/2010 | Bosch et al. |
| 7,906,136 B2 | 3/2011 | Wong et al. |
| 9,458,169 B2 | 10/2016 | Enlow et al. |
| 2001/0000521 A1 | 4/2001 | Bigg et al. |
| 2002/0013322 A1 | 1/2002 | Smith et al. |
| 2002/0026052 A1 | 2/2002 | Boschelli et al. |
| 2002/0107392 A1 | 8/2002 | Renhowe et al. |
| 2002/0147205 A1 | 10/2002 | Carter et al. |
| 2003/0032624 A1 | 2/2003 | Yang |
| 2003/0055049 A1 | 3/2003 | Kath et al. |
| 2003/0092721 A1 | 5/2003 | Pitts et al. |
| 2003/0092908 A1 | 5/2003 | Pitts et al. |
| 2003/0100573 A1 | 5/2003 | Wang et al. |
| 2003/0114452 A1 | 6/2003 | Adams et al. |
| 2003/0114486 A1 | 6/2003 | Metcalf et al. |
| 2003/0181472 A1 | 9/2003 | Clark et al. |
| 2003/0199491 A1 | 10/2003 | Hennequin |
| 2003/0212276 A1 | 11/2003 | Boschelli et al. |
| 2004/0063955 A1 | 4/2004 | Biediger et al. |
| 2004/0092535 A1 | 5/2004 | Barsanti et al. |
| 2004/0235848 A1 | 11/2004 | Okuzumi et al. |
| 2005/0009809 A1 | 1/2005 | Gerlach et al. |
| 2005/0009815 A1 | 1/2005 | Devita et al. |
| 2005/0026915 A1 | 2/2005 | Devita et al. |
| 2005/0038050 A1 | 2/2005 | Moore et al. |
| 2005/0054662 A1 | 3/2005 | Hennequin et al. |
| 2005/0058603 A1 | 3/2005 | Gao et al. |
| 2005/0085465 A1 | 4/2005 | Hennequin |
| 2005/0101617 A1 | 5/2005 | Wallace et al. |
| 2005/0124562 A1 | 6/2005 | Guiles et al. |
| 2005/0137399 A1 | 6/2005 | Cai et al. |
| 2005/0148607 A1 | 7/2005 | Suzuki et al. |
| 2005/0187247 A1 | 8/2005 | Berger et al. |

(Continued)

*Primary Examiner* — Heidi Reese
(74) *Attorney, Agent, or Firm* — K&L Gates LLP; Louis C. Cullman; Michelle Glasky Bergman

(57) ABSTRACT

Described herein are crystalline forms of Compound 1 useful for the prevention and treatment of angiogenic ocular conditions; methods of treating a disease comprising; processes for preparing; and kits comprising, the same.

Compound 1

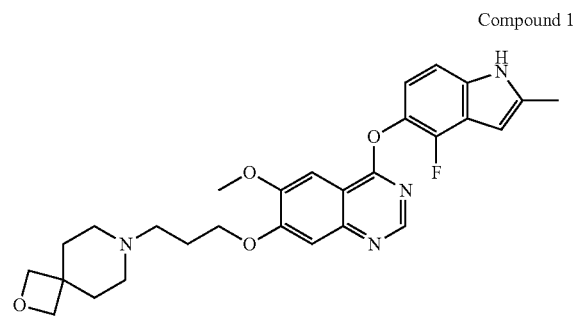

7 Claims, 2 Drawing Sheets

(56) References Cited

U.S. PATENT DOCUMENTS

| | | |
|---|---|---|
| 2005/0191359 A1 | 9/2005 | Goldshtein et al. |
| 2005/0239825 A1 | 10/2005 | Heise et al. |
| 2005/0245547 A1 | 11/2005 | Kim et al. |
| 2005/0256157 A1 | 11/2005 | Gesner et al. |
| 2005/0261307 A1 | 11/2005 | Cai et al. |
| 2005/0266067 A1 | 12/2005 | Sengupta et al. |
| 2005/0266090 A1 | 12/2005 | Prokop et al. |
| 2005/0282802 A1 | 12/2005 | Kostik et al. |
| 2006/0004017 A1 | 1/2006 | Stokes et al. |
| 2006/0025406 A1 | 2/2006 | Zembower et al. |
| 2006/0058325 A1 | 3/2006 | Mortlock |
| 2006/0058523 A1 | 3/2006 | Mortlock et al. |
| 2006/0079515 A1 | 4/2006 | Frost |
| 2006/0116357 A1 | 6/2006 | Heron et al. |
| 2006/0167026 A1 | 7/2006 | Nawa et al. |
| 2006/0223783 A1 | 10/2006 | Xu et al. |
| 2006/0241115 A1 | 10/2006 | Potashman et al. |
| 2006/0252777 A1 | 11/2006 | Kim et al. |
| 2006/0257487 A1 | 11/2006 | Owen et al. |
| 2006/0264460 A1 | 11/2006 | Green et al. |
| 2006/0270668 A1 | 11/2006 | Chew et al. |
| 2006/0270669 A1 | 11/2006 | Chew et al. |
| 2007/0032518 A1 | 2/2007 | Norman et al. |
| 2007/0054916 A1 | 3/2007 | Patel et al. |
| 2007/0059552 A1 | 3/2007 | Takeda et al. |
| 2007/0060608 A1 | 3/2007 | Vanderslice et al. |
| 2007/0060613 A1 | 3/2007 | Kim |
| 2007/0093432 A1 | 4/2007 | Yang |
| 2007/0129387 A1 | 6/2007 | McCabe |
| 2007/0149480 A1 | 6/2007 | Ghosh et al. |
| 2007/0149523 A1 | 6/2007 | Ehlert et al. |
| 2007/0178051 A1 | 8/2007 | Pruitt et al. |
| 2007/0196860 A1 | 8/2007 | Gee et al. |
| 2007/0213319 A1 | 9/2007 | Zembower et al. |
| 2007/0231821 A1 | 10/2007 | Bupp et al. |
| 2007/0299044 A1 | 12/2007 | Farng et al. |
| 2008/0027099 A1 | 1/2008 | Govek et al. |
| 2008/0096193 A1 | 4/2008 | Bupp et al. |
| 2008/0125448 A1 | 5/2008 | Qian et al. |
| 2008/0153799 A1 | 6/2008 | Laurent et al. |
| 2008/0159984 A1 | 7/2008 | Ben-Sasson |
| 2008/0175887 A1 | 7/2008 | Wang |
| 2008/0194468 A1 | 8/2008 | Bodor |
| 2008/0200464 A1 | 8/2008 | Bellon et al. |
| 2008/0221161 A1 | 9/2008 | Pinkerton et al. |
| 2008/0248125 A1 | 10/2008 | Irache Garreta et al. |
| 2008/0267876 A1 | 10/2008 | Benita et al. |
| 2008/0280917 A1 | 11/2008 | Albrecht et al. |
| 2008/0306053 A1 | 12/2008 | Tachdjian et al. |
| 2008/0312232 A1 | 12/2008 | Kim et al. |
| 2008/0318943 A1 | 12/2008 | Chang et al. |
| 2009/0036474 A1 | 2/2009 | Ple et al. |
| 2009/0047244 A1 | 2/2009 | Parsy et al. |
| 2009/0062279 A1 | 3/2009 | Marsais et al. |
| 2009/0062337 A1 | 3/2009 | Schwan et al. |
| 2009/0076044 A1 | 3/2009 | Qian et al. |
| 2009/0087493 A1 | 4/2009 | Dai et al. |
| 2009/0105211 A1 | 4/2009 | Bahceci et al. |
| 2009/0131461 A1 | 5/2009 | Davidson et al. |
| 2009/0221591 A1 | 9/2009 | Hartmann et al. |
| 2009/0253148 A1 | 10/2009 | Piper et al. |
| 2010/0015136 A1 | 1/2010 | Michel et al. |
| 2010/0048447 A1 | 2/2010 | Haetzelt et al. |
| 2010/0056506 A1 | 3/2010 | Huang et al. |
| 2010/0076045 A1 | 3/2010 | Castillo et al. |
| 2010/0093727 A1 | 4/2010 | Ning et al. |
| 2010/0168149 A1 | 7/2010 | Lavielle et al. |
| 2010/0204234 A1 | 8/2010 | Hartmann et al. |
| 2010/0222308 A1 | 9/2010 | Zhang et al. |
| 2010/0226931 A1 | 9/2010 | Valiante et al. |
| 2010/0290983 A1 | 11/2010 | Rabinow et al. |
| 2011/0053931 A1 | 3/2011 | Gaudino et al. |
| 2011/0104161 A1 | 5/2011 | Burgess et al. |
| 2011/0166168 A1 | 7/2011 | Buchmann et al. |
| 2011/0172186 A1 | 7/2011 | Behnke et al. |
| 2011/0275643 A1 | 11/2011 | Liou et al. |
| 2011/0306572 A1 | 12/2011 | Estok et al. |
| 2011/0319403 A1 | 12/2011 | Zhou et al. |
| 2012/0021897 A1 | 1/2012 | Iwata et al. |
| 2012/0121718 A1 | 5/2012 | Lai et al. |
| 2012/0214803 A1 | 8/2012 | Buhr et al. |
| 2012/0225875 A1 | 9/2012 | Jonczyk et al. |
| 2012/0232110 A1 | 9/2012 | Moy et al. |
| 2012/0252756 A1 | 10/2012 | Coffey et al. |
| 2012/0264715 A1 | 10/2012 | Takeuchi et al. |
| 2012/0264730 A1 | 10/2012 | Takeuchi et al. |
| 2012/0264732 A1 | 10/2012 | Takeuchi et al. |
| 2012/0289486 A1 | 11/2012 | Bodor |
| 2012/0292571 A1 | 11/2012 | Buesing et al. |
| 2012/0305852 A1 | 12/2012 | Anemian et al. |
| 2013/0102603 A1 | 4/2013 | Dorsch et al. |
| 2013/0109713 A1 | 5/2013 | Lavoie et al. |
| 2013/0116279 A1 | 5/2013 | Govek et al. |
| 2013/0123344 A1 | 5/2013 | Kristie et al. |
| 2013/0210844 A1 | 8/2013 | Gharat et al. |
| 2013/0245032 A1 | 9/2013 | Chen et al. |
| 2013/0281402 A1 | 10/2013 | Chen et al. |
| 2013/0324570 A1 | 12/2013 | Hansen et al. |
| 2013/0344165 A1 | 12/2013 | Boden et al. |
| 2014/0024661 A1 | 1/2014 | Zhou et al. |
| 2014/0142137 A1 | 5/2014 | Cohen et al. |
| 2014/0163037 A1 | 6/2014 | Guenther et al. |
| 2014/0228361 A1 | 8/2014 | Zhang et al. |
| 2014/0235548 A1 | 8/2014 | Zhou et al. |
| 2014/0235657 A1 | 8/2014 | Ong et al. |
| 2014/0239281 A1 | 8/2014 | Ise et al. |
| 2014/0294764 A1 | 10/2014 | Yoon et al. |
| 2014/0294973 A1 | 10/2014 | Kan et al. |
| 2014/0296136 A1 | 10/2014 | Rudd et al. |
| 2014/0315886 A1 | 10/2014 | Suzuki et al. |
| 2015/0125535 A1 | 5/2015 | Enlow et al. |
| 2016/0115176 A1 | 4/2016 | Enlow et al. |
| 2016/0235753 A1 | 8/2016 | Ong et al. |
| 2016/0257693 A1 | 9/2016 | Enlow et al. |

CRYSTALLINE FORMS OF THERAPEUTIC COMPOUNDS AND USES THEREOF

FIELD

This disclosure relates to crystalline forms of a therapeutic compound useful for treating diseases, including proliferative diseases and diseases associated with angiogenesis, such as cancer and macular degeneration.

BACKGROUND

Growth factors play an important role in angiogenesis, lymphangiogenesis, and vasculogenesis. Growth factors regulate angiogenesis in a variety of processes including embryonic development, wound healing, and several aspects of female reproductive function. Undesirable or pathological angiogenesis is associated with diseases including diabetic retinopathy, psoriasis, cancer, rheumatoid arthritis, atheroma, Kaposi's sarcoma, and hemangioma. Angiogenic ocular conditions represent the leading cause of irreversible vision loss in developed countries. In the United States, for example, retinopathy of prematurity, diabetic retinopathy, and age-related macular degeneration are the principal causes of blindness in infants, working age adults, and the elderly, respectively. Efforts have been developed to inhibit angiogenesis in the treatment of these conditions.

Therefore, there is a need for new therapeutic compositions for the treatment of diseases associated with the aberrant signaling of growth factors and diseases associated with angiogenesis, such as cancer, macular degeneration, and diabetic retinopathy.

SUMMARY

Compound 1 may be useful for the treatment of the proliferative diseases associated with angiogenesis, such as angiogenic ocular diseases. This disclosure relates to crystalline forms of Compound 1.

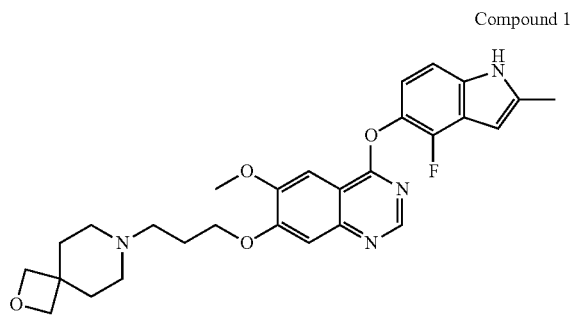 [SMILES: COc1cc2c(Oc3ccc4[nH]c(C)cc4c3F)ncnc2cc1OCCCN1CCC2(CC1)COC2]

Compound 1

In some embodiments, the crystalline form has an X-ray powder diffraction (XRPD) pattern with a largest peak at about 10-11 degrees 2θ.

Some embodiments include, a crystalline form of Compound 1 having an X-ray powder diffraction (XRPD) pattern with a largest peak at about 18-19 degrees 2θ.

Some embodiments include a process for preparing a crystalline form E described herein, comprising mixing Compound 1 and methanol.

Some embodiments include a process for preparing a crystalline form D described herein, comprising mixing Compound 1 and water at room temperature or at 40° C.

Some embodiments include a pharmaceutical composition comprising a crystalline form disclosed herein.

Some embodiments include a kit comprising the crystalline form disclosed herein, or the pharmaceutical composition disclosed herein.

Some embodiments include a method of treating a disease comprising administering to a subject in need thereof a therapeutically effective amount of the crystalline form or a pharmaceutical composition.

DETAILED DESCRIPTION

This description relates to crystal or crystalline forms of the compound 7-(3-(4-(4-fluoro-2-methyl-1H-indol-5-yloxy)-6-methoxyquinazolin-7-yloxy)propyl)-2-oxa-7-azaspiro[3.5]nonane, or a salt thereof, referred to herein as Compound 1 and shown below:

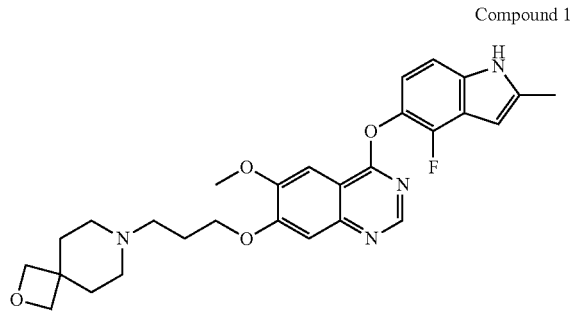 [SMILES: COc1cc2c(Oc3ccc4[nH]c(C)cc4c3F)ncnc2cc1OCCCN1CCC2(CC1)COC2]

Compound 1

In particular, two crystalline forms of Compound 1—crystalline form E and crystalline form D—are described herein.

Several X-ray powder diffraction (XRPD) patterns are depicted and described herein. As used herein, the "largest peak" refers to the peak in a diffraction pattern with the highest intensity. As used herein, the term "major intensity peak" includes any peak having an intensity that is in the top 20% of the peaks in a particular X-ray powder diffraction pattern.

Crystalline Form E

Crystalline form E has an XRPD pattern with a largest peak at about 10-11 degrees two theta (2θ). The diffraction pattern may also have a major intensity peak at about 10-11 degrees 2θ, about 15-16 degrees 2θ, about 18-19 degrees 2θ, about 23-23.5 degrees 2θ, and/or about 23.5-24 degrees 2θ, and may have other major intensity peaks.

Crystalline form E may be a solvate, such as a methanol solvate.

While there are many ways that crystalline form E may potentially be prepared, in some embodiments, crystalline form E may be prepared by stirring a slurry of amorphous of Compound 1 in methanol.

Crystalline Form D

Figure 2:
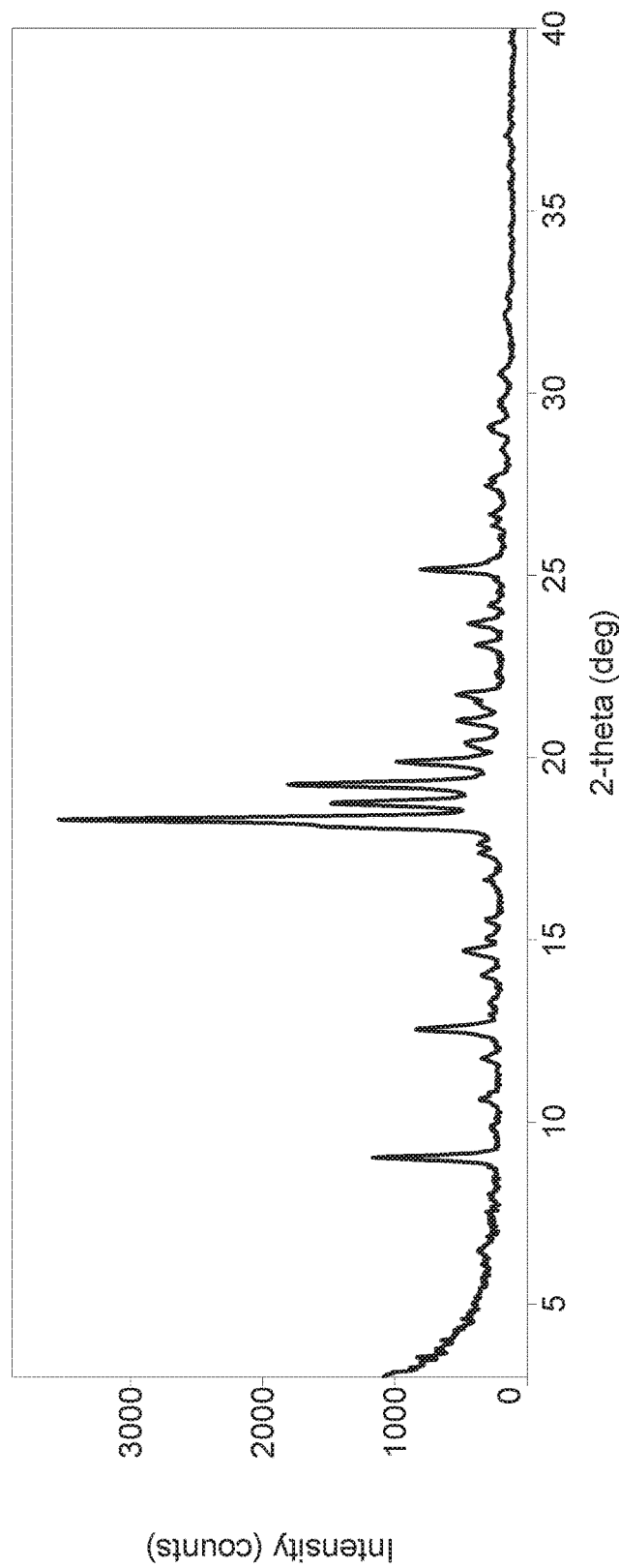
FIG. 2 depicts an XRPD pattern of crystalline form D.

Crystalline form D has an XRPD pattern with a largest peak at about 18-19 degrees 2θ (e.g., about 18.28 degrees 2θ). The diffraction pattern may also have a major intensity peak at about 8.5-9.5 degrees 2θ (e.g., about 9.02 degrees 2θ), about 18.0-18.2 degrees 2θ (e.g., about 18.08 degrees 2θ), about 18.6-18.8 degrees 2θ (e.g., about 18.72 degrees 2θ), about 19-19.5 degrees 2θ (e.g., about 19.25 degrees 2θ), about 19.5-20.0 degrees 2θ (e.g., about 19.86 degrees 2θ), and/or about 25.0-25.5 degrees 2θ (e.g., about 25.13 degrees 2θ), and may have other major intensity peaks. In some embodiments, crystalline form D has an XRPD pattern as shown in FIG. 2.

Crystalline form D may be a hydrate.

While there are many ways that crystalline form D may be prepared, crystalline form D may be prepared by stirring a slurry of amorphous of Compound 1 or crystalline form E of Compound 1 in water.

Methods of Treatment

Compound 1 may be used for treating and/or preventing a disease associated with aberrant signaling of a growth factor, such as vascular endothelial growth factor (VEGF). In some embodiments, Compound 1 in a crystalline form may be used to treat a disease associated with abnormal angiogenesis, such as cancer, benign neoplasm, atherosclerosis, hypertension, inflammatory disease, rheumatoid arthritis, macular degeneration (AMD), choroidal neovascularization, retinal neovascularization, and diabetic retinopathy. In certain embodiments, Compound 1 is used to treat cancer (e.g., an ocular cancer). In certain embodiments, Compound 1 is used to treat macular degeneration.

Compound 1 may also be used to treat or prevent a proliferative disease, such as cancer, ocular disease (e.g., retinopathy, age-related macular degeneration (AMD), corneal neovascularization, diabetic macular edema, retinal vein occlusion etc.).

The term "ocular disease" or "ocular disorder" includes any eye disease and/or disorder. For example, ocular diseases can be disorders of the eyelid, lacrimal system and orbit, disorders of conjunctiva, disorders of sclera, cornea, iris and ciliary body, disorders of choroid, disorders of retina, glaucoma, disorders of optic nerve and visual pathways, ocular neovascularization diseases or disorders, ocular inflammatory diseases, or disorders of ocular muscles. Additionally, ocular disease can also refer to discomfort following injury, surgery, or laser treatment. Diseases and disorders of the eye or ocular diseases include, but are not limited to, retinopathy, diabetic retinopathy, retinal vein occlusion, macular degeneration, age-related macular degeneration, dry eye syndrome, blepharitis, inflammatory meibomian gland disease, uveitis, allergic conjunctivitis, glaucoma, macular edema, diabetic macular edema, cystoid macular edema, and rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals.

The term "age-related macular degeneration" or "AMD" includes an ocular disease which usually affects older adults and results in a loss of vision in the center of the visual field (the macula) because of damage to the retina. It occurs in "dry" and "wet" forms. It is a major cause of blindness and visual impairment in older adults (>50 years).

Macular degeneration can make it difficult or impossible to read or recognize faces, although enough peripheral vision remains to allow other activities of daily life. The macula is the central area of the retina, which provides the most detailed central vision. In the dry (nonexudative) form, cellular debris called drusen accumulate between the retina and the choroid, and the retina can become detached. In the wet (exudative) form, which is more severe, blood vessels grow up from the choroid behind the retina, and the retina can also become detached. It can be treated with laser coagulation, and with medication that stops and sometimes reverses the growth of blood vessels. Macular degeneration includes some macular dystrophies affecting younger subjects as well as age-related macular degeneration (AMD or ARMD), which is more commonly known. AMD begins with characteristic yellow deposits (drusen) in the macula, between the retinal pigment epithelium and the underlying choroid. Most patients with these early changes (referred to as age-related maculopathy) have good vision. Patients with drusen can go on to develop advanced AMD. The risk is considerably higher when the drusen are large and numerous and associated with disturbance in the pigmented cell layer under the macula. Recent research suggests that large and soft drusen are related to elevated cholesterol deposits and may respond to cholesterol-lowering agents.

The term "macular edema" refers to the ocular diseases cystoid macular edema (CME) or diabetic macular edema (DME). CME is an ocular disease which affects the central retina or macula of the eye. When this condition is present, multiple cyst-like (cystoid) areas of fluid appear in the macula and cause retinal swelling or edema. CME may accompany a variety of diseases such as retinal vein occlusion, uveitis, and/or diabetes. CME commonly occurs after cataract surgery. DME occurs when blood vessels in the retina of patients with diabetes begin to leak into the macula. These leaks cause the macula to thicken and swell, progressively distorting acute vision. While the swelling may not lead to blindness, the effect can cause a severe loss in central vision.

The term "glaucoma" refers to an ocular disease in which the optic nerve is damaged in a characteristic pattern. This can permanently damage vision in the affected eye and lead to blindness if left untreated. It is normally associated with increased fluid pressure in the eye (aqueous humor). The term ocular hypertension is used for patients with consistently raised intraocular pressure (IOP) without any associated optic nerve damage. Conversely, the term normal tension or low tension glaucoma is used for those with optic nerve damage and associated visual field loss but normal or low IOP. The nerve damage involves loss of retinal ganglion cells in a characteristic pattern. There are many different subtypes of glaucoma, but they can all be considered to be a type of optic neuropathy. Raised intraocular pressure (e.g., above 21 mmHg or 2.8 kPa) is the most important and only modifiable risk factor for glaucoma. However, some may have high eye pressure for years and never develop damage, while others can develop nerve damage at a relatively low pressure. Untreated glaucoma can lead to permanent damage of the optic nerve and resultant visual field loss, which over time can progress to blindness.

The term "uveitis" refers to an inflammatory disease of the uvea, the vascular layer of the eye sandwiched between the retina and the white of the eye (sclera). The uvea extends toward the front of the eye and consists of the iris, choroid layer and ciliary body. Uveitis includes anterior uveitis, intermediate uveitis, and posterior uveitis. A most common type of uveitis is an inflammation of the iris called iritis (anterior uveitis). Uveitis may also occur at the posterior segment of the eye (e.g., at the choroid). Inflammation of the uvea can be recurring and can cause serious problems such as blindness if left untreated (accounts for 10% of blindness globally). Early diagnosis and treatment are important to prevent the complications of uveitis.

The term "dry eye" or "dry eyes" includes an ocular disease in which there are insufficient tears to lubricate and nourish the eye. Tears are necessary for maintaining the health of the front surface of the eye and for providing clear vision. Patients with dry eyes either do not produce enough tears or have a poor quality of tears. Dry eye is a common and often chronic problem, particularly in older adults. With each blink of the eyelids, tears are spread across the front surface of the eye, known as the cornea. Tears provide lubrication, reduce the risk of eye infection, wash away foreign matter in the eye, and keep the surface of the eyes smooth and clear. Excess tears in the eyes flow into small drainage ducts, in the inner corners of the eyelids, which drain in the back of the nose. Tears are produced by several glands (e.g., lacrimal gland) in and around the eyelids. Tear production tends to diminish with age, with various medical conditions, or as a side effect of certain medicines. Environmental conditions such as wind and dry climates can also affect tear volume by increasing tear evaporation. When the normal amount of tear production decreases or tears evaporate too quickly from the eyes, symptoms of dry eye can develop. The most common form of dry eyes is due to an inadequate amount of the water layer of tears. This condition, called keratoconjunctivitis sicca (KCS), is also referred to as "dry eye syndrome."

The term "diabetic retinopathy" includes retinopathy (i.e., a disease of the retina) caused by complications of diabetes, which can eventually lead to blindness. Diabetic retinopathy may cause no symptoms, mild vision problems, or even blindness. Diabetic retinopathy is the result of microvascular retinal changes. Hyperglycemia-induced intramural pericyte death and thickening of the basement membrane lead to incompetence of the vascular walls. These damages change the formation of the blood-retinal barrier and also make the retinal blood vessels become more permeable. The pericyte death is caused when hyperglycemia persistently activates protein kinase C-δ (PKC-δ, encoded by Prkcd) and p38 mitogen-activated protein kinase (MAPK) to increase the expression of a previously unknown target of PKC-δ signaling, Src homology-2 domain-containing phosphatase-1 (SHP-1), a protein tyrosine phosphatase. This signaling cascade leads to PDGF receptor-dephosphorylation and a reduction in downstream signaling from this receptor, resulting in pericyte apoptosis. Small blood vessels, such as those in the eye, are especially vulnerable to poor control over blood sugar. An overaccumulation of glucose and/or fructose damages the tiny blood vessels in the retina. During the initial stage, called "nonproliferative diabetic retinopathy" (NPDR), most patients do not notice any change in their vision. Early changes that are reversible and do not threaten central vision are sometimes termed simplex retinopathy or background retinopathy. As the disease progresses, severe nonproliferative diabetic retinopathy enters an advanced, "proliferative diabetic retinopathy" (PDR) stage when blood vessels proliferate. The lack of oxygen in the retina causes fragile, new, blood vessels to grow along the retina and in the clear, gel-like vitreous humor that fills the inside of the eye, which may result in bleeding, cloudy vision, retina damage, or tractional retinal detachment.

Treatment or prevention of a disease may be accomplished by administering Compound 1 to a mammal, such as a human being, in need thereof.

Pharmaceutical Compositions

A crystalline form of Compound 1, such as a crystalline form E or a crystalline form D, hereafter referred to as a "crystalline form," may be present in a pharmaceutical composition that may further comprise a pharmaceutically acceptable excipient.

A crystalline form of Compound 1 may be intended for delivery in a subject.

Excipients

A pharmaceutically acceptable excipient or pharmaceutically acceptable carrier may include a non-toxic, inert solid, semi-solid or liquid filler, diluent, encapsulating material or formulation auxiliary of any suitable type. Any pharmaceutically acceptable excipient may be used herein. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on the route of administration as described below, the pharmaceutical agent being delivered, time course of delivery of the agent, etc.

Non-limiting examples of polymers which can be included in the disclosed pharmaceutical compositions include polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D, L-lactide-co-PEO-co-D, L-lactide), poly(D, L-lactide-co-PPO-co-D, L-lactide), polyalkyl cyanoacrylate, polyurethane, poly-L-lysine (PLL), hydroxypropyl methacrylate (HPMA), poly (ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate.

Route of Administration

Pharmaceutical compositions containing the particles described herein may be administered to a subject via any route known in the art. These include, but are not limited to, oral, sublingual, nasal, injection (e.g., intravenous, intradermal, subcutaneous, intramuscular), rectal, vaginal, intraarterial, intracisternally, intraperitoneal, intravitreal, periocular, topical (e.g., ocular or dermal, such as by powders, creams, ointments, or drops), buccal, and inhalational administration. In some embodiments, compositions described herein may be administered parenterally as injections (intravenous, intramuscular, or subcutaneous), drop infusion preparations, or suppositories. The route of administration and the effective dosage to achieve the desired biological effect may be determined by the agent being administered, the target organ, the preparation being administered, time course of administration, disease being treated, intended use, etc.

Moreover, the pharmaceutical compositions may be administered parenterally as injections (intravenous, intramuscular, or subcutaneous), drop infusion preparations, or suppositories. For ophthalmic applications, the pharmaceutical compositions may be administered by injection (e.g., intraocular, conjunctival, subconjunctival, intrastromal, intravitreal, or intracameral), or by the local or ophthalmic mucous membrane route, the pharmaceutical compositions may be administered topically, such as solutions, suspensions (e.g., eye drops), gels, or ointments.

In some embodiments, an effective amount of Compound 1 in a crystalline form may vary from about 0.001 mg/kg to about 20 mg/kg in one or more dose administrations for one or several days (depending on the mode of administration). In certain embodiments, the effective amount per dose varies from about 0.001 mg/kg to about 20 mg/kg, from about 0.01 mg/kg to about 10 mg/kg, from about 0.1 mg/kg to about 5 mg/kg, from about 0.01 mg/kg to about 0.5 mg/kg, and from about 0.5 mg/kg to about 2 mg/kg, about 2 mg/kg to about 4 mg/kg, about 4 mg/kg to about 10 mg/kg, or any dose amount bounded by or between any of these values.

EXAMPLES

Example 1

Synthesis of Compound 1

Compound 1 may be prepared by the method described in U.S. Pat. No. 9,458,169, which is hereby incorporated by reference for its description of the synthesis of Compound 1.

Example 2

Preparation of Amorphous Compound 1

The synthesized Compound 1 (6.25 g) was suspended in water (300 mL). Hydrochloric acid (1M, 20 mL) was added. All material dissolved to form a light yellow solution. The solution was filtered through a disk filter (1 μm) and placed under high vacuum with magnetic stirring for 10 minutes. While stirring a saturated sodium bicarbonate (300 mL) was added over 10 minutes. The high vacuum was applied for additional 10 minutes and the solution was stirred for 30 minutes under normal pressure. The solid precipitate was filtered off on a sintered glass funnel (F porosity). The solid was washed with water (300 mL) and dried by passage of vacuum for 1 hour. The solid was further dried under high vacuum overnight. The material obtained was a white amorphous solid (5.45 g).

Example 3

Preparation of Crystalline Form E of Compound 1

Crystalline form E was prepared by stirring a slurry of amorphous Compound 1 in methanol.

In one instance, amorphous Compound 1 (30.8 mg) was added into a 4-mL scintillation vial with screw-top. To the vial was added a magnetic stir bar and methanol (500 μL). The vial was capped and the suspension in the vial was allowed to stir at ambient temperature (about 22° C.) with 300 RPM speed for 2 hours.

The solid material was collected by centrifuge filtration and the filtrate was discarded. The centrifuge filter tube was then lightly covered and dried under high vacuum for approximately 17 hours. The recovered dry solid (26.7 mg) was analyzed by x-ray powder diffraction (XRPD), which showed a unique powder pattern that was assigned as crystalline form E. This experiment was successfully reproduced three times as indicated in Table 1.

TABLE 1

Summary of conversion to crystalline form E from amorphous Compound 1.

| Experiment | Amorphous initially used (mg) | Volume of methanol added (uL) | Initial Concentration (mg/mL) | Crystalline Form E Recovered (mg) | Recovery Yield by mass |
|---|---|---|---|---|---|
| 1 | 30.8 | 0.5 | 61.6 | 26.7 | 92.2% |
| 2 | 29.6 | 0.5 | 59.2 | 25.5 | 91.6% |
| 3 | 29.7 | 0.5 | 59.4 | 26.6 | 95.2% |

Properties of Crystalline Form E

Figure 1:
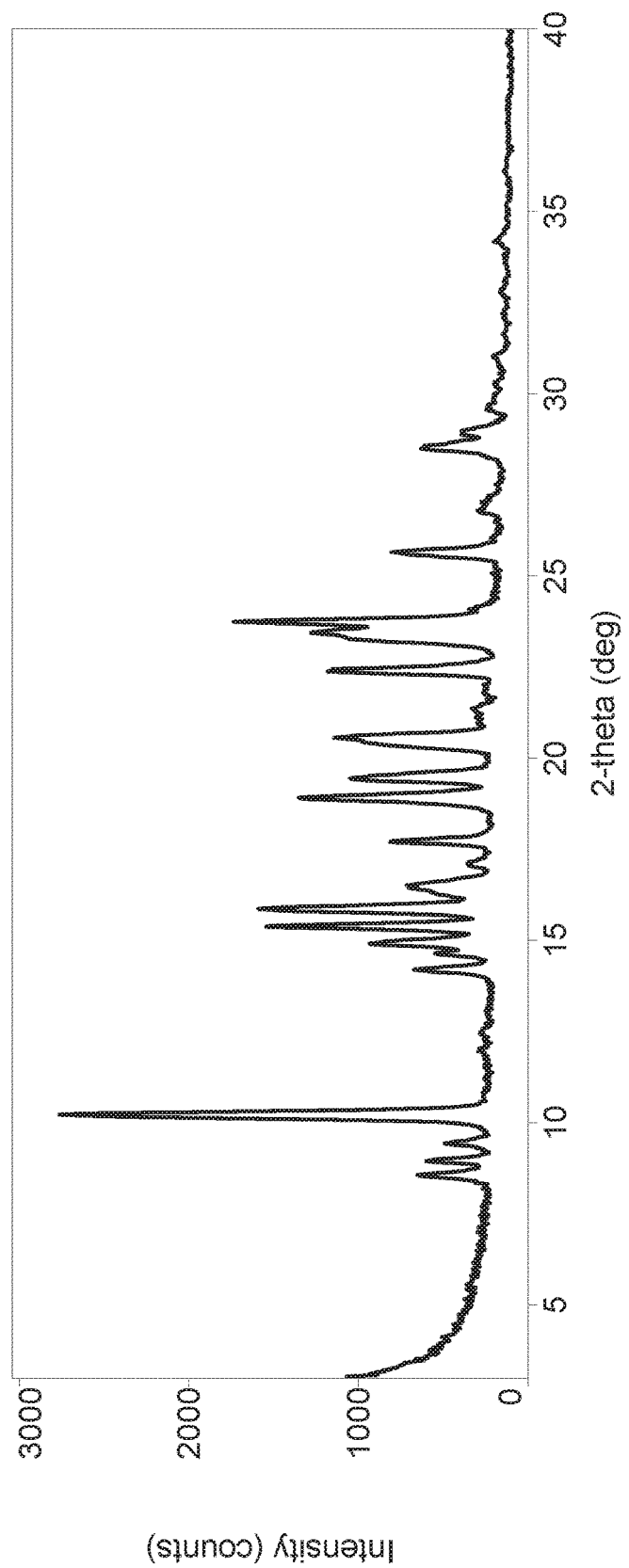
FIG. 1 depicts the x-ray powder diffraction (XRPD) pattern of crystalline form E.

The XRPD pattern of crystalline form E is illustrated in FIG. 1. The peaks in degrees 2θ, the corresponding d-spacing values, and relative intensity (%) from the XRPD pattern of crystalline form E are listed in Table 2.

TABLE 2

XRPD peak listing of crystalline form E.

| Peak No. | Position ± 0.2° [2θ] | d-spacing ± 0.2 [Å] | Relative Intensity [%] |
|---|---|---|---|
| 1 | 8.55 | 10.33 | 12.85 |
| 2 | 8.95 | 9.87 | 8.72 |
| 3 | 9.43 | 9.37 | 6.27 |
| 4 | 10.22 | 8.65 | 100.00 |
| 5 | 14.19 | 6.23 | 14.09 |
| 6 | 14.65 | 6.04 | 9.27 |
| 7 | 14.90 | 5.94 | 28.70 |
| 8 | 15.38 | 5.76 | 40.99 |
| 9 | 15.86 | 5.58 | 52.79 |
| 10 | 16.50 | 5.37 | 32.26 |
| 11 | 17.07 | 5.19 | 3.65 |
| 12 | 17.69 | 5.01 | 16.53 |
| 13 | 18.90 | 4.69 | 45.03 |
| 14 | 19.43 | 4.57 | 35.00 |
| 15 | 20.33 | 4.36 | 12.97 |
| 16 | 20.57 | 4.31 | 39.09 |
| 17 | 21.36 | 4.16 | 5.34 |

TABLE 2-continued

XRPD peak listing of crystalline form E.

| Peak No. | Position ± 0.2° [2θ] | d-spacing ± 0.2 [Å] | Relative Intensity [%] |
|---|---|---|---|
| 18 | 22.36 | 3.97 | 35.40 |
| 19 | 23.24 | 3.82 | 11.49 |
| 20 | 23.46 | 3.79 | 67.26 |
| 21 | 23.75 | 3.74 | 45.38 |
| 22 | 25.63 | 3.47 | 26.16 |
| 23 | 26.76 | 3.33 | 8.83 |
| 24 | 28.52 | 3.13 | 22.86 |
| 25 | 28.93 | 3.08 | 10.61 |
| 26 | 29.56 | 3.02 | 5.47 |
| 27 | 34.19 | 2.62 | 3.74 |

Thermographic Analysis (TGA) was found to exhibit a mass loss of 8.88%. Since solution ¹H NMR confirmed the presence of methanol in neat crystalline form E, the TGA data suggests that the mass loss is possibly due to loss of methanol.

Example 4

Preparation of Crystalline Form D

Crystalline form D was prepared by stirring a slurry of amorphous Compound 1 in water.

In one instance, amorphous Compound 1 (30.1 mg) was added into a 4-mL scintillation vial with screw-top. To the vial was added a magnetic stir bar and water (500 µL). The vial was capped and the suspension was allowed to stir at ambient temperature (about 22° C.) with 300 RPM speed for 2.5 hours.

The solid material was collected by centrifuge filtration and the filtrate was discarded. The centrifuge filter tube was lightly covered then dried under high vacuum for approximately 1 hour. The recovered dry solid (25.7 mg) was analyzed by XRPD, which showed a unique powder pattern that was assigned as crystalline form D. This experiment was successfully reproduced four times as indicated in Table 3.

TABLE 3

Summary of conversion to crystalline form D from amorphous Compound 1.

| Experiment | Amorphous initially used (mg) | Volume of methanol added (uL) | Initial Concentration (mg/mL) | Crystalline Form D Recovered (mg) | Recovery Yield by mass |
|---|---|---|---|---|---|
| 1 | 30.1 | 0.5 | 60.2 | 25.7 | 91.4% |
| 2 | 29.8 | 0.5 | 59.6 | 25 | 89.9% |
| 3 | 30.8 | 0.5 | 61.6 | 26.3 | 91.5% |
| 4 | 30.1 | 0.5 | 60.2 | 24.3 | 86.5% |

Crystalline form D was also prepared by stirring a slurry of crystalline form E of Compound 1 in water.

In one instance, crystalline form E of Compound 1 (30.6 mg) was added into a 4-mL scintillation vial with screw-top. To the vial was added a magnetic stir bar and water (300 µL). The vial was capped and the suspension was allowed to stir at 40° C. with 300 RPM speed for two hours.

The solid material was collected by centrifuge filtration and the filtrate was discarded. The centrifuge filter tube was then lightly covered and dried under high vacuum for approximately 30 minutes. The recovered dry solid (28.2 mg) was analyzed by XRPD, which showed a unique powder pattern that was assigned as crystalline form D. This experiment was successfully reproduced three times as indicated in Table 4.

TABLE 4

Summary of conversion to crystalline form D from crystalline form E.

| Sample | Crystalline form E initially used (mg) | Volume of water added (uL) | Initial Concentration (mg/mL) | Crystalline Form D Recovered (mg) | Recovery Yield by mass |
|---|---|---|---|---|---|
| 1 | 30.6 | 300 | 102 | 28.2 | 93.4% |
| 2 | 30.9 | 300 | 103 | 28.4 | 91.2% |
| 3 | 30.2 | 300 | 101 | 27.4 | 90.1% |

Properties of Crystalline Form D

The XRPD pattern of crystalline form D is illustrated in FIG. 2. The peaks in two-theta, the corresponding d-spacing values, and relative intensity (%) in the XRPD pattern of form D are listed in Table 5.

TABLE 5

XRPD peak listing of crystalline form D.

| Peak No. | Position ± 0.2° [2θ] | d-spacing ± 0.2 [Å] | Relative Intensity [%] |
|---|---|---|---|
| 1 | 6.47 | 13.66 | 5.7 |
| 2 | 9.02 | 9.80 | 26.1 |
| 3 | 10.60 | 8.34 | 4.2 |
| 4 | 11.74 | 7.53 | 3.3 |
| 5 | 12.50 | 7.07 | 25.9 |
| 6 | 13.28 | 6.66 | 4.8 |
| 7 | 14.03 | 6.31 | 5.1 |
| 8 | 14.69 | 6.03 | 10.9 |
| 9 | 18.08 | 4.90 | 39.5 |
| 10 | 18.28 | 4.85 | 100.0 |
| 11 | 18.72 | 4.74 | 42.2 |
| 12 | 19.25 | 4.61 | 56.8 |
| 13 | 19.86 | 4.47 | 24.5 |
| 14 | 20.40 | 4.35 | 9.3 |
| 15 | 20.97 | 4.23 | 8.7 |
| 16 | 21.42 | 4.14 | 5.4 |
| 17 | 21.71 | 4.09 | 8.1 |
| 18 | 23.08 | 3.85 | 4.3 |
| 19 | 23.67 | 3.76 | 7.3 |
| 20 | 24.14 | 3.68 | 1.7 |
| 21 | 25.13 | 3.54 | 24.8 |
| 22 | 26.67 | 3.34 | 5.5 |
| 23 | 27.49 | 3.24 | 8.5 |
| 24 | 29.03 | 3.07 | 6.9 |
| 25 | 29.71 | 3.00 | 3.7 |
| 26 | 30.50 | 2.93 | 2.7 |

The foregoing description details specific methods and compositions that can be employed to make and use the compounds described herein, and represents the best mode contemplated. However, it is apparent for one of ordinary skill in the art that other compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, the foregoing description should not be construed as limiting the scope of the claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consist-ing of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A crystalline form of Compound 1:

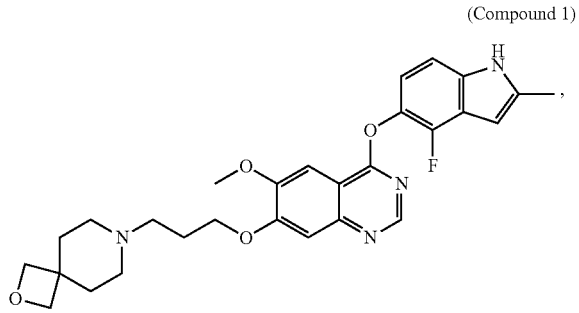 [SMILES: COc1cc2c(Oc3ccc4[nH]c(C)cc4c3F)ncnc2cc1OCCCN1CCC2(CC1)COC2]

(Compound 1)

wherein the crystalline form has an X-ray powder diffraction (XRPD) pattern comprising peaks at 8.5-9.5 degrees 2θ, 18-19 degrees 2θ, 19-19.5 degrees 2θ, and 25.0-25.5 degrees 2θ.

2. The compound of claim 1, wherein the crystalline form is a hydrate.

3. A process for preparing a crystalline form of claim 1, comprising:
   mixing an amorphous form of Compound 1 and water at room temperature or mixing crystalline form E of Compound 1 in water at 40° C. to form a suspension; and
   recovering the crystalline form from the suspension.

4. A pharmaceutical composition comprising the crystalline form of claim 1 and a pharmaceutically acceptable carrier.

5. The pharmaceutical composition of claim 4, wherein the pharmaceutical composition is suitable for topical administration.

6. The pharmaceutical composition of claim 4, wherein the pharmaceutical composition is suitable for injection.

7. The pharmaceutical composition of claim 4, wherein the pharmaceutical composition is suitable for delivery to the eye.

* * * * *